(12) United States Patent
Tu et al.

(10) Patent No.: US 7,153,299 B1
(45) Date of Patent: Dec. 26, 2006

(54) OPTICAL APPARATUS FOR DETECTING AND TREATING VULNERABLE PLAQUE

(75) Inventors: Hosheng Tu, Newport Beach, CA (US); Winston Z. Ho, Hacienda Heights, CA (US)

(73) Assignee: Maxwell Sensors Inc., Santa Fe Springs, CA (US)

( * ) Notice: Subject to any disclaimer, the term of this patent is extended or adjusted under 35 U.S.C. 154(b) by 304 days.

(21) Appl. No.: 10/877,867

(22) Filed: Jun. 26, 2004

Related U.S. Application Data

(63) Continuation-in-part of application No. 10/373,539, filed on Feb. 24, 2003, now Pat. No. 7,004,911.

(51) Int. Cl.
*A61B 18/24* (2006.01)
*A61B 18/22* (2006.01)
*A61N 5/067* (2006.01)

(52) U.S. Cl. .............. 606/15; 128/898; 606/1; 607/89

(58) Field of Classification Search ............ 128/898; 600/549; 607/88–94
See application file for complete search history.

(56) References Cited

U.S. PATENT DOCUMENTS

| | | | |
|---|---|---|---|
| 5,444,803 A | 8/1995 | Kim et al. | |
| 5,924,997 A | 7/1999 | Campbell | |
| 6,018,160 A | 1/2000 | Bennion et al. | |
| 6,054,449 A | 4/2000 | Robinson et al. | |
| 6,096,030 A | 8/2000 | Ortiz | |
| 6,248,117 B1 * | 6/2001 | Blatter | 606/153 |
| 6,475,159 B1 | 11/2002 | Casscells et al. | |
| 6,514,214 B1 | 2/2003 | Kokate et al. | |
| 6,623,494 B1 * | 9/2003 | Blatter | 606/153 |
| 6,716,178 B1 * | 4/2004 | Kilpatrick et al. | 600/504 |
| 6,716,410 B1 | 4/2004 | Witztum et al. | |
| 2003/0103995 A1 | 6/2003 | Hamblin et al. | |
| 2004/0044304 A1 | 3/2004 | Hill et al. | |
| 2004/0057900 A1 | 3/2004 | Edwards et al. | |
| 2004/0071632 A1 | 4/2004 | Witztum et al. | |
| 2004/0092830 A1 | 5/2004 | Scott et al. | |
| 2004/0093044 A1 | 5/2004 | Rychanvsky et al. | |

OTHER PUBLICATIONS

Presentation at 2003 TCT meeting, Washington D.C. Paul Yeck "Photodynamic modulation of vulnerable plaque with antrin".
Review : Current Perspective I. Morteza Naghavi etal. Circulation 2003; 108: 1664-1672.
Review: Current Perspective II. Morteza Naghavi etal. Circulation 2003; 108: 1772-1778.

* cited by examiner

*Primary Examiner*—Henry M Johnson, III

(57) ABSTRACT

An optical apparatus and methods for monitoring temperature enabling detection and treatment of a vulnerable plaque of a patient comprising an elongate catheter, a plurality of outer optical fibers deployably disposed within the lumen of the catheter and suitably expandable in an outwardly radial manner configured for forming a basket shape, the outer fibers having at least one optical grating along an axis of the fiber wherein the at least one optical grating reflects a certain wavelength or intensity of the light beam, the certain wavelength or intensity of the reflected light beam being correlated to known temperature, and a longitudinal middle optical fiber emitting a light energy suitable for photodynamic therapy.

20 Claims, 12 Drawing Sheets

OPTICAL APPARATUS FOR DETECTING AND TREATING VULNERABLE PLAQUE

CROSS-REFERENCE TO RELATED APPLICATIONS

This application is a continuation-in-part application of U.S. patent application Ser. No. 10/373,539, filed Feb. 24, 2003, now U.S. Pat. No. 7,004,911, entire contents of which are incorporated herein by reference.

FIELD OF THE INVENTION

The present invention is generally related to an optical thermal mapping device for measuring the intravascular vessel temperature in vivo with high spatial and temperature resolution. More particularly, the present invention relates to an optical thermal mapping device comprising multiple optical fibers with optical gratings for monitoring the thermal distribution of, and detecting and photodynamically treating vulnerable plaques within a blood vessel.

BACKROUND OF THE INVENTION

Vulnerable plaques are atherosclerotic plaques associated with erosion and ulceration that prone to rupture leading to acute embolization and thrombus. Until recently, physicians believed that most heart attacks were caused by a gradual buildup of atherosclerotic plaque in the arteries of the heart that eventually impeded blood flow. In fact, up to half of all sudden, out-of-hospital cardiac deaths occur in people with no prior diagnosis of heart disease and over two-thirds of heart attack suffers have blockages in their arteries considered to be clinically insignificant in terms of plaque burden and percent stenosis.

Most ruptured plaques are characterized by a large lipid pool and a thin fibrous cap with macrophage infiltration. On the other hand, calcified plaque deposits typically comprise hard material that restricts blood flow in a blood vessel. But, atherosclerotic plaque may also comprise combinations of soft and hard materials. The main difference between a soft vulnerable plaque and a hard stable plaque lies in the risk for a vulnerable plaque to rupture suddenly. The risk of plaque rupture is greatest when the fibrous cap is very thin or the plaque lipid pool is very large.

The buildup of plaque in the blood vessels is sometimes referred to as atherosclerosis, or hardening of the arteries. Atherosclerosis often begins as a small injury to an artery wall. This injury triggers a cascade of injury and response, inflammation, and healing, which may ultimately lead to the narrowing of the artery. It is generally believed that inflammation in an arterial plaque is the result of a series of biochemical and mechanical changes in the arterial wall. The inflammatory cells collect the debris of the damaged tissue resulting in a core of lipid, including macrophages or foam cells and necrotic tissue that is covered by a thin fibrous cap of scar tissue. If the fibrous cap becomes weakened, eroded, or is subjected to excessive mechanical stress, it may rupture and expose the thrombogenic damaged endothelium and metabolic byproducts to the blood stream that causes blood clotting. If the resulting blood clot is severe enough, it may occlude the artery. If this obstruction persists in a coronary artery, a myocardial infarction or angina may result.

Many vulnerable plaque deposits do not obstruct the flow of blood through the blood vessels. Vulnerable plaques are often undetectable using conventional techniques such as angiography. However, a plaque may rupture suddenly and form a blood clot in the blood vessel lumen causing a blockage and causes heart attack and death. Recently, inflammation has been recognized being associated with the formation and progression of vulnerable plaques. An increase in tissue temperature at a lesion is thought to be caused by the response of the immune system to inflammation and an increase in metabolic activity involved in the healing process. It has been observed that the inflamed necrotic core of a vulnerable plaque maintains itself at a temperature which may be a fraction of a degree to a few degrees higher than the surrounding tissue. Vulnerable plaques are generally characterized by hemodynamically insignificant, variable in size, not calcified, and undetectable with standard anatomic imaging methods.

The inability of common diagnostic methodologies, such as coronary angiography that is the current gold standard technique for diagnosing coronary vessel obstructions, to detect vulnerable plaque has led to a major rush to develop new methods to detect, characterize and treat patients with these types of deposits. Unlike the typical occlusive atherosclerotic lesion, vulnerable plaque deposits are associated with a compensatory enlargement of the vessel wall known as positive lumen remodeling. Selected intravascular imaging techniques for vulnerable plaque include angioscopy, intravascular ultrasound, thermography, optical coherence tomography, elastography, magnetic resonance imaging, nuclear imaging, electrical impedance imaging, shear stress imaging, photonic spectroscopy, and the like. Among them, catheter-based intravascular thermography is the most promising one, which is based on the premise that vulnerable plaques are hotter than surrounding normal tissue and that by measuring these temperature elevation, physicians can determine the exact location and extent of disease.

Casscells and associates (Current Opinion in Cardiology 2002;17:656–662) reported mechanism of heat production in atherosclerotic plaques by a high metabolic rate in the areas of macrophage accumulation, of which a sub-population strongly expresses mitochondrial uncoupling proteins. The uncoupling proteins are homologs of thermogenin, which is responsible for thermogenesis in brown fat tissue. Further, they measured temperature of living samples with a thermistor and found that plaques showed several regions in which the surface temperatures varied reproducibly by 0.2° C. to 0.3° C. Infrared thermographic images also revealed heterogeneity in temperature among the plaques.

U.S. Pat. No. 5,924,997 to Campbell, entire contents of which are incorporated herein by reference, discloses an intravascular catheter system capable of mapping thermal variations in the temperature of atherosclerotic plaque by a plurality of thermal sensors fixedly attached along the catheter. The thermal sensors are mounted on the catheter shaft and soldered to a conductor while each sensor needs a conductor. The spacing of the mechanical thermal sensors arrangement allows only limited sensors to be placed within a unit length.

U.S. Pat. No. 6,292,695 to Webster, Jr. et al., entire contents of which are incorporated herein by reference, discloses a basket shaped catheter with a plurality of electrodes on each expandable member of the basket, while each electrode may comprise a thermal sensor for temperature monitoring. The spacing of the electrodes with mechanical thermal sensors arrangement allows only limited sensors to be placed within a unit length on each expandable member of the basket.

U.S. Pat. No. 6,450,971 to Andrus et al., entire contents of which are incorporated herein by reference, discloses a balloon catheter having temperature responsive material designed to exhibit at least one predetermined color when the material is in contact with an object having an elevated temperature, wherein a light detector positioned to indirectly detect the color change indicative of suspected lesion. The Andrus et al. balloon catheter uses a moving light detector to map multiple lesion sites within a blood vessel.

U.S. Pat. No. 6,475,159 to Casscells et al, entire contents of which are incorporated herein by reference, discloses an infrared heat-sensing catheter using an infrared fiberoptic system at the tip of the catheter to locate a single inflamed, heat-producing atherosclerotic plaque. The Casscells et al. catheter uses a dragging method to map multiple lesion sites within a blood vessel.

U.S. Pat. No. 6,514,214 to Kokate et al., entire contents of which are incorporated herein by reference, discloses a catheter with at least one temperature sensor disposed proximate to the distal end of the elongate shaft adapted to contact an inner surface of the blood vessel. The Kokate et al. catheter uses a dragging method to map multiple lesion sites within a blood vessel.

None of the above-identified patents discloses a thermal sensing means for measuring a plurality of contiguous points without dragging the device for area thermal mapping. In a co-pending patent application Ser. No. 10/373,539, filed Feb. 24, 2003, there is disclosed an optical thermal mapping device and methods for monitoring the thermal profiles enabling detecting vulnerable plaques within a blood vessel on a real time basis. The thermal mapping of vulnerable plaques using at least one optical fiber with multiple optical gratings are disclosed therein without dragging the device for area thermal mapping.

Optical fibers are hair thin strands of glass that guide light. The optical fiber has an inner core surrounded by an outer cladding. In order to guide light, the core refractive index is higher than the cladding index. A fiber grating, which the periodic structure of the refractive index is formed inside the core of a fiber, is widely used in the field of fiber-optic communication for wavelength management. The optical grating reflects or transmits a certain portion, wavelength (bandwidth) or intensity, of the light along optical fibers. A fiber Bragg grating is based on the interference of multiple reflection of a light beam in a fiber segment whose index of refraction varies periodically along the length of the fiber. Variations of the refractive index constitute discontinuities that emulate a Bragg structure. If the spacing of the index periods is equal to one half of the wavelength of the light, then the waves will interfere constructively (the round trip of each reflected wave is one wavelength) and a large reflection will occur from the periodic array. Optical signals whose wavelengths are not equal to one half the spacing will travel through the periodic array unaffected.

A periodic variation of the refractive index is formed by exposing the core, such as germanosilicate, of the fiber to an intense ultraviolet (UV) optical interference pattern or mask that has a periodicity equal to the periodicity of the grating to be formed. When the fiber is exposed to an intensive UV pattern, structural defects are formed and thus a permanent variation of the refractive indexes having the same periodicity with the UV pattern. The condition for strong reflection of Bragg wavelength is $\lambda=2\times n\times d$. Where n is the effective refractive index, and d is Bragg spacing or grating period. Both n and d change with changes in temperature due to thermal-optic and thermal expansion effects.

The merits of optical fiber sensors include immunity to electromagnetic interference, high flexibility, remote sensing capability, smaller size of sensing element, lightweight, and easy to fabricate. Optical fiber sensors have been developed for chemical, strain, temperature and pressure sensing, and smart structure inspection. Various fiber-grating configurations have been developed for sensor application. Depending on its configuration, in general, it can be classified as direct and indirect sensors. Direct sensors measure the environmental effects surrounding the grating. Indirect sensors measure the environmental effects at the tip of the fiber and use fiber grating for wavelength management. The sensing signal is obtained through either a transmission or reflection mode. In some aspect of the present invention, it is provided direct fiber grating as direct sensors in a reflection mode.

Fiber gratings reflect light of particular bandwidth, and can act as high-performance optical thermal sensor. The reflected bandwidths are extremely narrow because of the long path lengths possible in optical fibers. Therefore, a minute temperature change surrounding the fibers changes the effective refractive index and grating's periods, thus modulating their reflective wavelength or intensity. When multiple gratings are created in an optic fiber, a multi-point sensor can be monitored simultaneously.

Fiber-grating technologies have been proven and demonstrated with excellent sensing abilities for temperature, pressure, stress and various chemicals detection. They also exhibit extremely long-term stability, and minimal optical losses. Several prior art devices have been described for the performance of a number of optical fiber grating sensors. U.S. Pat. No. 5,627,927 discloses an interferometer fiber grating for sensing the environmental effect at the termination of the fiber. U.S. Pat. No. 6,072,922 discloses a cryogenic fiber optical sensor by introducing additional thermal strain in the fiber to enhance sensor sensitivity. U.S. Pat. No. 5,444,803 discloses a fiber-optic device includes fiber grating and mode stripper to admit only one mode for sensor application. U.S. Pat. No. 6,018,160 discloses an apparatus using two optical gratings for sensing aircraft skin temperature and/or strain. The above-referred patents, U.S. Pat. Nos. 5,627,927, 6,072,922 5,444,803, and 6,018,160, entire contents of all being incorporated herein by reference, disclose fiber-grating technology suitably applicable in the present invention.

Although many prior art patents are related to optical grating sensor, none of them discloses a medical device system and methods combining multiple grating in multiple fibers formed in a basket configuration for intravascular temperature measurement in vivo. Furthermore, there is a clinical need for an optical apparatus system with dual capabilities of diagnosing vulnerable plaque via thermal mapping and treating vulnerable plaque within a blood vessel via photodynamic therapy in a one-step single operation.

SUMMARY OF THE INVENTION

In accordance with preferred embodiments of the present invention, an optical thermal basket catheter is provided for intravascular measurement of the temperature of a vessel wall. In one aspect of the present invention, it is provided an optical thermal basket catheter comprising an elongate catheter sheath having a lumen, a distal sheath end, and a proximal sheath end; a plurality of optical fibers deployably disposed within the lumen of the catheter sheath, each fiber having a distal fiber portion, a distal fiber end and a proximal fiber end, wherein the plurality of distal fiber portions is suitably expandable in an outwardly radial manner adapted for forming a basket shape and for contacting at least a portion of the vessel wall. Each fiber has at least one optical grating along an axis of the fiber; and a light source has a light beam, wherein the light beam is coupled into the plurality of optical fibers, wherein the at least one optical grating reflects a certain wavelength or intensity of the light beam, the certain wavelength or intensity of the reflected light beam being correlated to the temperature of the portion of the vessel wall.

Another object of this invention is to provide a ready to use, highly sensitive and accurate catheter-based optical fiber sensor system for detecting vulnerable plaque. Thermographic images reveals heterogeneity in temperature profiles among the vulnerable plaques.

Another object of this invention is to provide a ready to use, highly sensitive and accurate device-based optical fiber sensor probe for detecting inflammation in coronary arteries or tissue regions such as a breast or a heart, wherein the probe is a catheter, a cannula or a hollow needle with side opening. In some aspect, it is provided an optical thermal device for monitoring temperature of a tissue region of a patient comprising an elongate tubular element comprising at least one optical fiber that contacts the tissue region; the at least one optical fiber having at least one optical grating along an axis of the fiber; and a light source having a light beam, wherein the light beam is coupled into the at least one optical fiber. The at least one optical grating along the axis of the fiber reflects a certain wavelength or intensity of the light beam, the certain wavelength or intensity of the reflected light beam being correlated to the temperature of the tissue region.

Another object of this invention is to combine a 4-French or smaller catheter with an expandable and externally controllable basket with multiple build-in flexible optical fibers, each fiber with multiple gratings, for suitably accessing an intravascular vessel and measuring the local temperature distribution of the vessel wall.

Another object of this invention is to provide an optical thermal device or an optical thermal basket catheter by using optical fiber gratings with thermal resolution of 0.001° C. to 5.0° C., preferably between 0.01° C. and 1.0° C.

It is a further object of the present invention to provide an optical thermal device or an optical thermal basket catheter by using optical fiber gratings having a length between 0.2 and 40 mm.

In still another aspect of the present invention, it is provided a method for monitoring temperature of a tissue region of a patient, the method comprising deploying an elongate tubular element into contacting the tissue region, wherein the elongate tubular element comprises at least one optical fiber. The fiber has at least one optical grating along an axis of the fiber, and a light source having a light beam is coupled into the at least one optical fiber; the optical grating reflecting a certain wavelength or intensity of the light beam, and the certain wavelength or intensity of the reflected light beam being correlated to the temperature of the tissue region.

The present optical fiber medical device has the advantages of simple, real-time, and easy operation. The probe also provides accurate and reproducible results. It should be understood, however, that the detail description and specific examples, while indicating preferred embodiments of the present invention, are given by way of illustration and not of limitation. Further, as will become apparent to those skilled in the art, the teaching of the present invention can be applied to medical devices for measuring temperature at a variety of body parts.

Some aspects of the invention provide an optical apparatus for treating tissue of a patient comprising: an elongate tubular element having a lumen, a distal end, and a proximal end; a support scaffold structure deployable out of the distal end of the tubular element, wherein the support scaffold structure comprises a plurality of basket arms extendable outwardly for fixing or stabilizing the support scaffold in place when deployed, the support scaffold structure having a longitudinal middle optical fiber that emits light; and a light source having a light beam, wherein the light beam is coupled into the middle optical fiber.

Some aspects of the invention provide a method for treating a tissue region of a patient, the method comprising: a) providing an elongate tubular catheter into contacting the tissue region, wherein the elongate tubular catheter comprises a plurality of peripheral optic fibers in a support scaffold structure that is radially expandable and a middle optic fiber, each fiber having at least one optical grating along the axis of the fiber, wherein the middle fiber further comprises a light transmission zone configured for photodynamic therapy; b) monitoring a temperature of the tissue region, wherein a light source having a light beam is coupled into each optical fiber; the at least one optical grating reflecting a certain wavelength or intensity of the light beam, and the certain wavelength or intensity of the reflected light beam being correlated to the temperature; c) administering a therapeutically effective amount of at least one photosensitizer composition, wherein the photosensitizer composition is localized to the tissue region; d) light activating the photosensitizer composition to produce a phototoxic species, wherein the activating light is transmitted from the middle fiber; and e) treating the tissue region photodynamically.

Further, some aspects of the invention relate to an optical thermal basket catheter for monitoring temperature of a vessel wall of a patient comprising: a) an elongate catheter sheath having a lumen, a distal sheath end, and a proximal sheath end; b) a plurality of outer optical fibers deployably disposed within the lumen of the catheter sheath, each outer fiber having a distal fiber portion, a distal fiber end and a proximal fiber end, wherein the plurality of distal fiber portions is suitably expandable in an outwardly radial manner configured for forming a basket shape and for contacting at least a portion of the vessel wall, each outer fiber having at least one optical grating along an axis of the fiber; c) a longitudinal middle optical fiber spaced about equally from each expanded outer fiber, wherein the middle fiber emits a light energy suitable for photodynamic therapy; and d) a light source having a light beam, wherein the light beam is coupled into the plurality of outer and middle optical fibers, wherein the at least one optical grating reflects a certain wavelength or intensity of the light beam, the certain wavelength or intensity of the reflected light beam being correlated to known temperature.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY MBODIMENTS

The preferred embodiments of the present invention described below relate particularly to an optical apparatus having both diagnostic and therapeutic functions. The diagnostic function of the apparatus comprises at least one optical fiber with multiple optical gratings for simultaneously monitoring the thermal profile of and detecting vulnerable plaque within a blood vessel. The therapeutic function of the apparatus comprises at least one optical fiber within a support scaffold for providing adequate light energy to activate photodynamic therapy onto the photosensitized vulnerable plaque. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Figure 1:
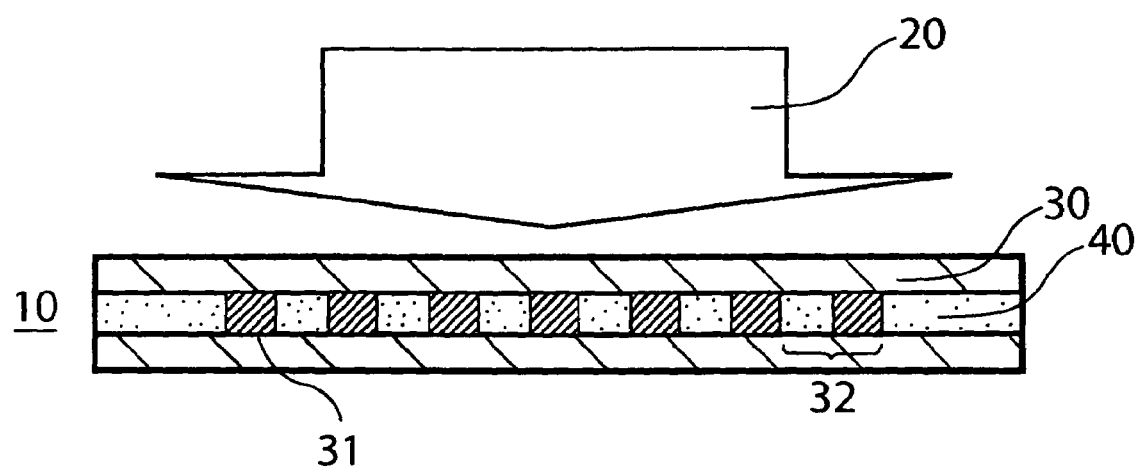
FIG. 1 is a fiber with a Bragg grating made by a UV interference pattern.

The optic fiber grating principles are briefly described herein for reference. The creation of high performance optical components by photolithographically writing periodic variations in the refractive index—"Bragg grating"—directly into the cores of conventional silica-based fibers. Regardless of the method used, the interference pattern must be of high quality, with uniform periodicity, high contrast, and sharp edges. The UV periodicity, as shown in FIG. 1, is formed by means of one of several optical methods (for example, UV mask, diffraction, interferometry, or the like) that generate an interference pattern of alternating minima and maxima of light intensity. The UV source 20 is provided by an excimer laser that operates at a wavelength in the 157–351 nm. The UV or near UV light pattern transmits through the cladding 30 and creates an index perturbation (n) 31 with a periodicity 32 in the core 40 of the fiber 10 that depends on the wavelength band in which the grating is designed to operate.

The grating reflectivity, R, for a given mode at enter wavelength ($\lambda$) is given by $$R = \tan h^2[\pi L n \eta(V)/\lambda]$$

Where L is the length of the grating, n is the magnitude of index perturbation, and $\eta$ (V) a function of fiber parameter V that represents the fraction of the integrated mode intensity contained in the core 40. The core diameter of the single mode fiber is typically less than 10 µm, while the total fiber diameter is approximately 0.1–2 mm. A smaller optic fiber of less than 100 µm may also be useful in certain medical applications.

Figure 2:
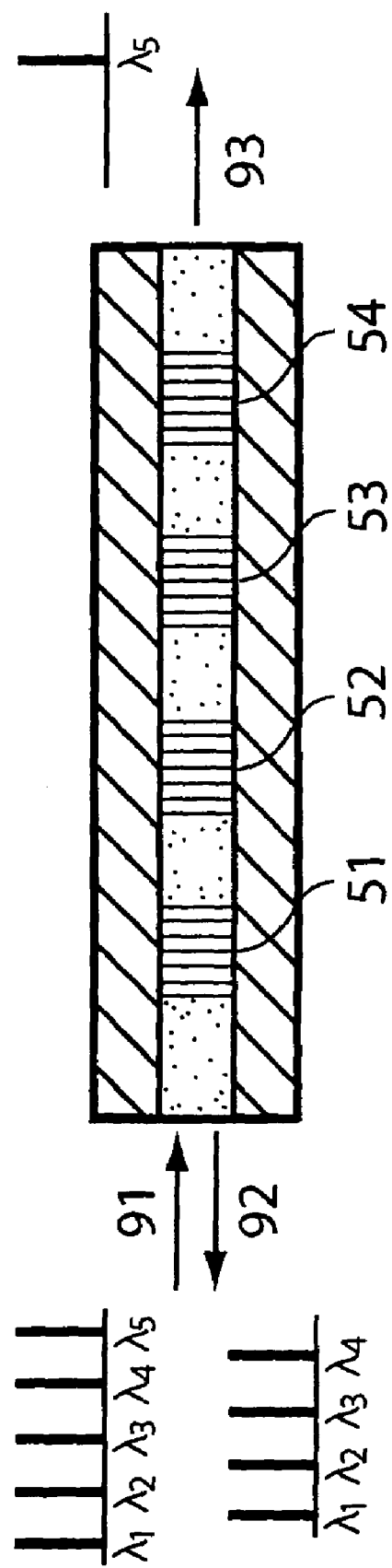
FIG. 2. is a cross section view of an optical fiber with multiple gratings, each grating with specific grating period reflecting a specific wavelength or bandwidth of the light.
Figure 3:
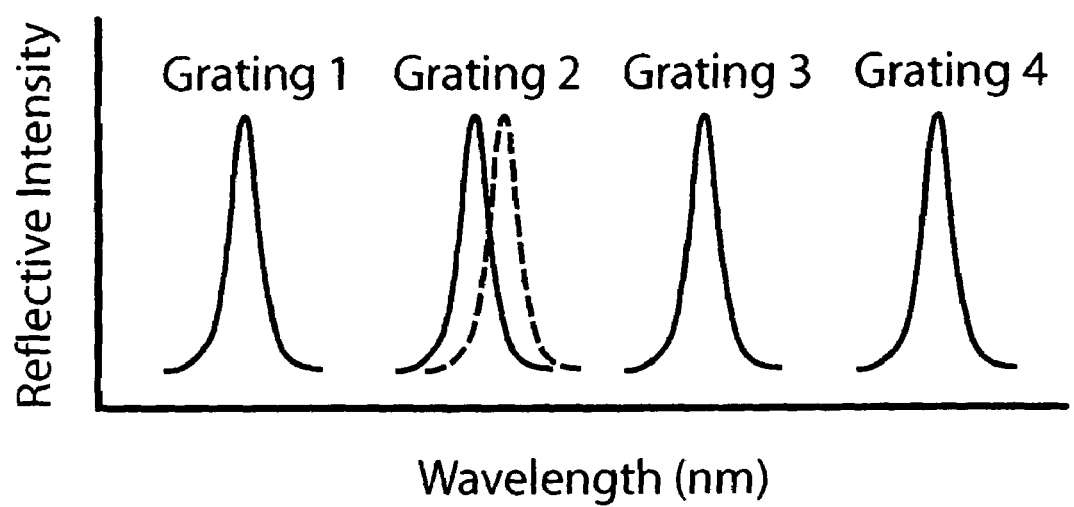
FIG. 3 shows multiple reflected wavelengths of the light from fiber gratings in a single optical fiber.
Figure 4:
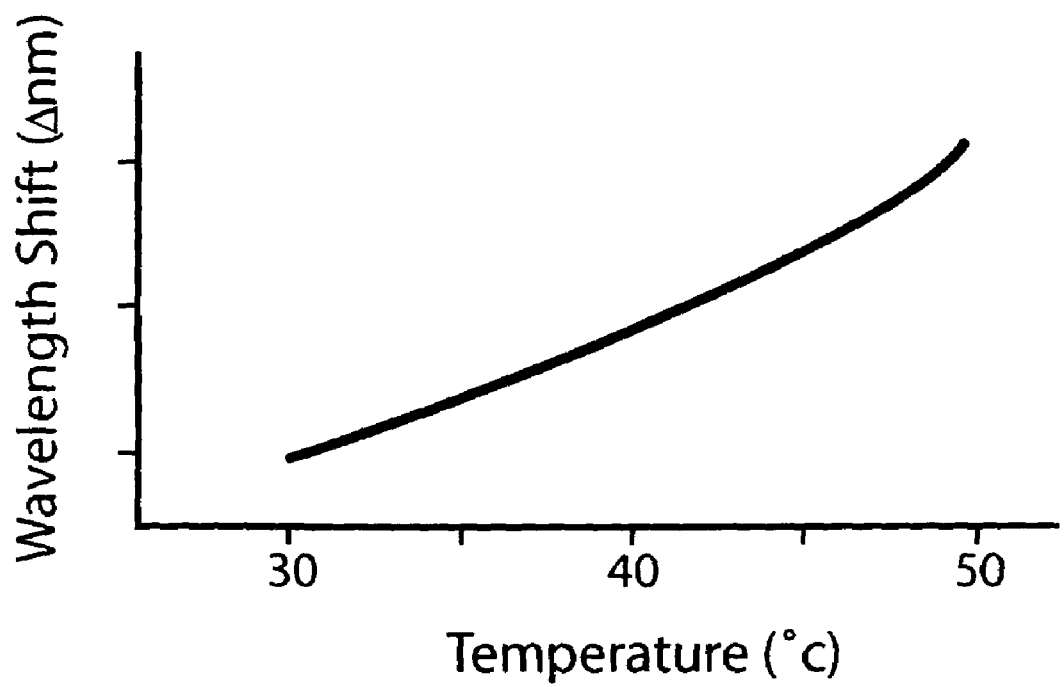
FIG. 4 is an illustrative graph shows a relationship between the wavelength shift and the temperature in the range of body temperature (30–50° C.).

Multiplexing of several grating 51, 52, 53, 54, as shown in FIG. 2, written in the same fiber 10 allows the creation of a distributed sensor capable of measuring the spatial profile of a temperature quantity. Each grating 51, 52, 53, 54, fabricated with different periodicity 32, reflects a specific wavelength. For illustration purposes, when a light beam 91 (with $\lambda_1$ to $\lambda_5$) from a broadband light source, an ultra wideband light source, or multiple-wavelength light source 98 (shown in FIG. 6) is input into the fiber, the multiple gratings reflect a first portion 92 ($\lambda_1$ to $\lambda_4$) and transmit a second portion 93 ($\lambda_5$) of the light depending on the effective index of the grating. Therefore, by monitoring the shift of a specific reflected wavelength, for example, as shown in grating 2 of the FIG. 3, the local temperature in the vessel wall at that grating can be correlatively measured externally. The total length of each grating is about 1 to 5 mm, and the reflectivity can be greater than −20 db. FIG. 4 shows an example of the correlated wavelength shift versus temperature at 37° C. in the range of human body temperature. The actual correlative relationship between the wavelength shift and the temperature of a specific fiber device system could be calibrated and established when the fibers are in a simulated operating shape, configuration and conditions.

The temperature resolution of the intrinsic silica core fiber Bragg grating is approximately 0.01 nm/° C. To obtain a resolution of 0.1° C., the spectrum analyzer must resolve the shift of the reflected wavelength to an accuracy of about 0.001 nm. Various methods are commonly used to increase temperature resolution. The first method is to apply temperature sensitive materials or polymers, such as PMMA, onto the cladding 30 at grating area, thus leads to a large temperature change or a larger temperature coefficient (n/T). The second method to enhance the temperature resolution is to use long-period grating. For typical Bragg grating, the grating periodicity (d) 32 is 0.5–10 µm, while for long period fiber grating (LPG), the periodicity can be as large as several hundred micrometers. The larger grating periodicity, d, in LPG will lead to a larger wavelength shift, $\lambda$. The higher order resonant peaks of LPG are very sensitive to its ambient refractive index. The wavelength shift of long period grating can be two to three orders of magnitude larger than that of Bragg grating. An LPG-based temperature sensor can easily achieve a resolution of about 0.01° C. or less.

Figure 5:
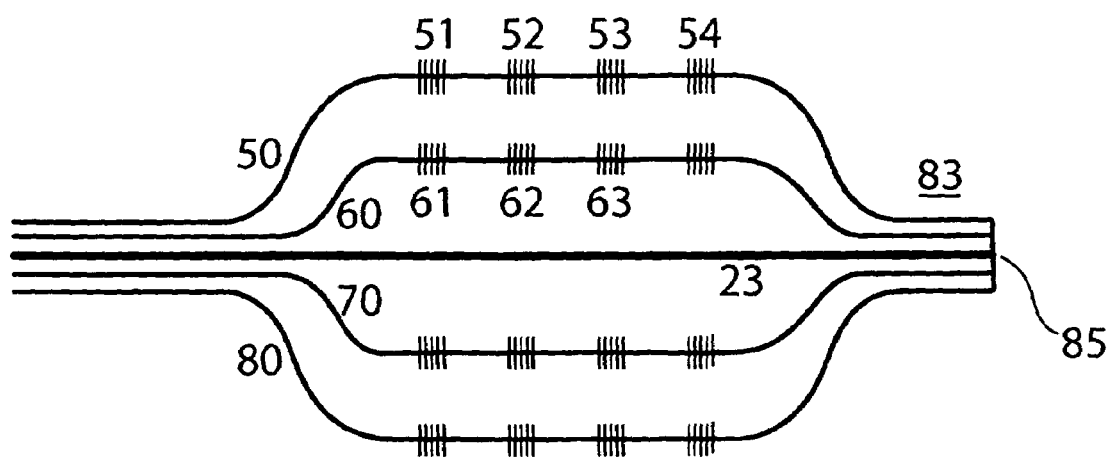
FIG. 5 shows the schematic diagram of a basket catheter with multiple optical fibers with multiple gratings for mapping the temperature distribution in a blood vessel.

FIG. 5 shows a distal portion basket arrangement of an optical thermal basket catheter loaded with multiple small and flexible optical fibers 50, 60, 70, 80, and each fiber is incorporated with multiple optical grating elements 51, 52, 53, 54, 61, 62, 63. A 3 or 4 French catheter or smaller with an expandable and externally controllable basket arrangement 21 can support 4 to 10 fibers depending on the design dimension and configuration. One method to deploy and radially expand the optical fiber basket is to utilize a highly flexible pulling wire 23 (also shown in FIG. 8A). In one embodiment, the tip 85 of the pulling wire 23 is secured to the tip bundle 83 of the flexible optical fibers 50, 60, 70, 80.

To enhance the outward expansion property, the optical fibers may suitably be slightly preshaped. In some aspect of the present invention, the basket catheter may comprise an inflatable balloon sized and configured to expand the fibers radially outward during the deployment and temperature sensing state. In one further aspect of the present invention, each of the fibers may be supported intimately by an expandable wire during the deployment and temperature sensing state. The basket catheter 19 permits good thermal contact of the optical grating elements on the optical fiber with the arterial wall. Each optical fiber sensors (that is, optical grating elements) are sized, configured and suitably located on the optical fiber enabling optimal contact with the target inner surface of a blood vessel, allowing monitoring of temperature upon expansion and in contact with the vulnerable plaque. The total sensing length in each fiber is approximately 2–5 cm. The length of the optical fiber is comparable to the length of the catheter. By using an optical thermal basket catheter system, it does not need to drag the catheter for mapping a whole region of interest.

Figure 6:
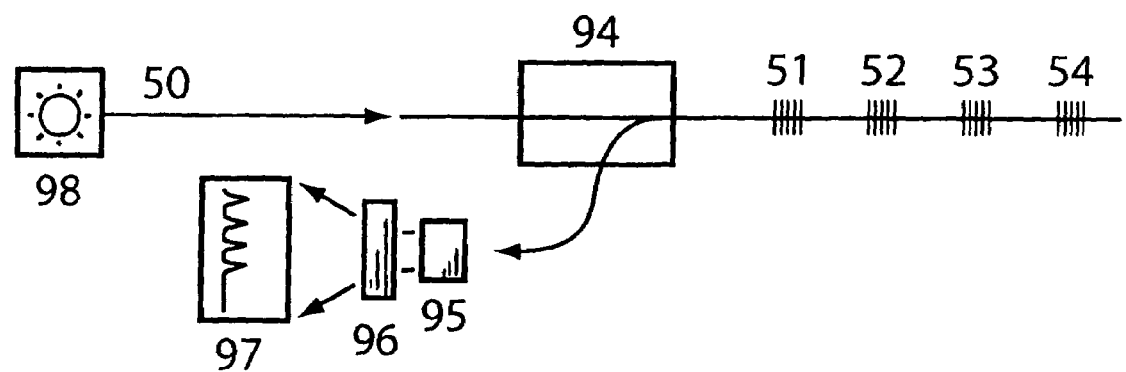
FIG. 6 shows the optoelectronic components of the optical thermal device system of the present invention for reflective wavelength measurement.

The optical thermal basket catheter system, as shown in FIG. 6, is integrated with a light source 98, a fiber splitting coupler 94, wavelength diffraction elements 96, and an optical signal detection system 97. Light from a broadband light-emitting diode (LED) or an ultra wideband light source travels through a single-mode fiber 50 to reach the grating 51, 52, 53, 54. Diode lasers, such as broadband diode lasers (1.3–1.55 µm) that cover the fiber communication wavelengths, are also available. Some lamp sources, such as a tungsten lamp, which are broadband light sources that cover the entire near infrared range, are also suitable as a continuous light source. Though the light source has a broad bandwidth; the reflected light from the grating is relatively narrow. The reflected light propagates back in the same fiber 50 and is coupled into a detection fiber by an optical coupler 94. Optical fiber couplers are used extensively in optical fiber communication systems. The most common couplers are fused fiber and directional coupler, which split the optical signal from one fiber into two fibers with different intensity ratio. The signal demultiplexing is constructed with a focusing/collimating lens 95, a diffraction grating 96, and a two dimensional CCD (charge coupled device) array 97.

The spectral peaks associated with each grating are physically separated by the diffraction grating 96 and illuminated on the CCD 97. The movement of the peak on CCD is related to the peak shift due to temperature change originated from fiber grating. When multiple signal fibers are aligned linearly in front of the entrance of the diffraction grating 96, a 2-D CCD provides the ability to simultaneously monitor multiple reflection spectra from multiple fibers. The detector 97 is interfaced through an analog-to-digital converter to an advanced signal processor in a computer. The real-time data acquisition software supports digital processing with a thermal resolution of 0.001° C. The temperature distributions obtained from the multiple sensors offer a thermographic mapping of the entire vessel walls. The circumferential and longitudinal thermal profiles of the vessel wall can also be displayed. The system is calibrated under simulated operating conditions to remove other non-thermal effects. In general, the data acquisition and analysis of the optical parameters are well known to an ordinary person who is skilled in the art.

Figure 7:
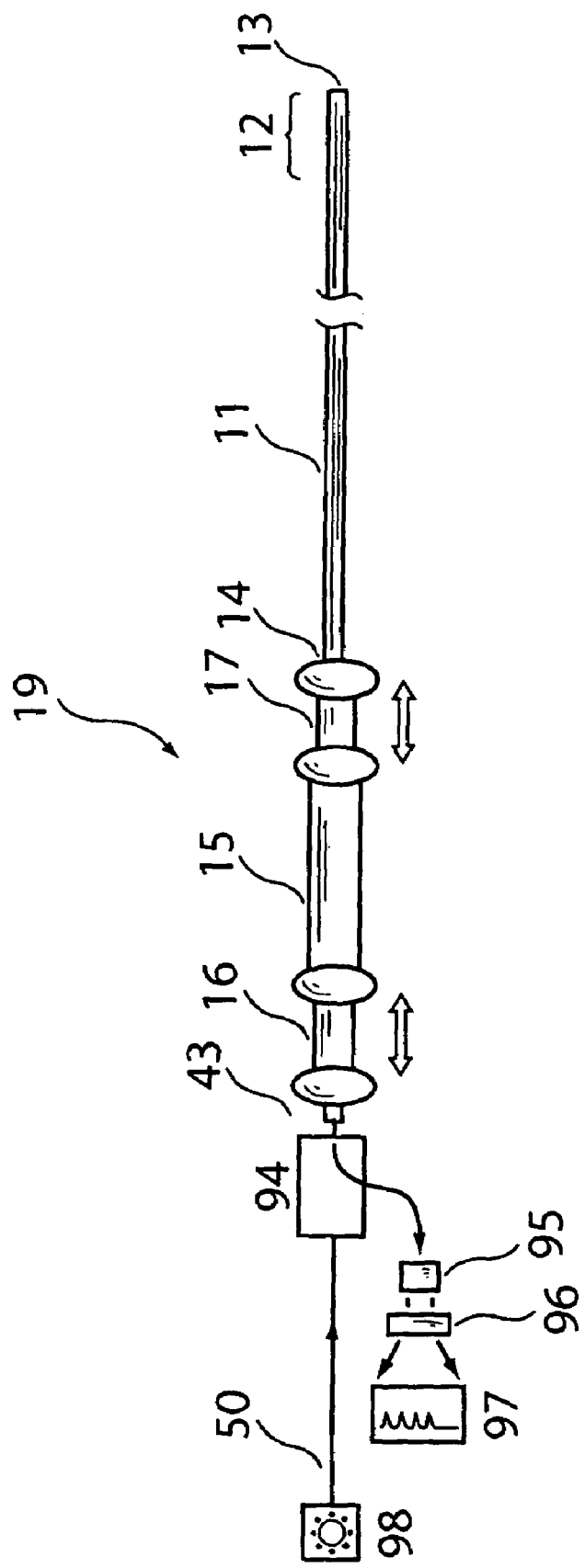
FIG. 7 is an overall view of the optical thermal device system having a deployable optical fiber assembly arrangement and the optoelectronic components, constructed in accordance with the principles of the present invention.

FIG. 7 shows an overall view of the optical thermal device system having a deployable optical fiber assembly arrangement and the optoelectronic components, constructed in accordance with the principles of the present invention. As shown in FIG. 7, one preferred embodiment of the thermal device system comprises an elongate tubular element (for example, a catheter shaft, a cannula, or a hollow needle) 11, the catheter shaft having a distal section 12, a shaft distal end 13, a shaft proximal end 14, and at least one lumen 18 extending between the shaft proximal end 14 and the shaft distal end 13, wherein the at least one lumen 18 may have at least one opening 71 at the shaft distal end 13 of the catheter shaft 11. A handle 15 is attached to the shaft proximal end 14 of the catheter shaft 11, wherein the handle 15 has a cavity for allowing at least one fiber 50, 60, 70, 80 and/or the pulling wire 23 to pass through.

In some aspect of the present invention, the optical thermal medical device 19 is for monitoring temperature of a tissue region of a patient without a need for dragging the device along the tissue wall. The device comprises an elongate tubular element comprising at least one optical fiber that contacts the tissue region; the at least one optical fiber having at least one optical grating along an axis of the fiber; and a light source having a light beam, wherein the light beam is coupled into the at least one optical fiber; wherein the at least one optical grating along the axis of the fiber reflects a certain wavelength or intensity of the light beam, the certain wavelength or intensity of the reflected light beam being correlated to the temperature of the tissue region.

Figure 8A:
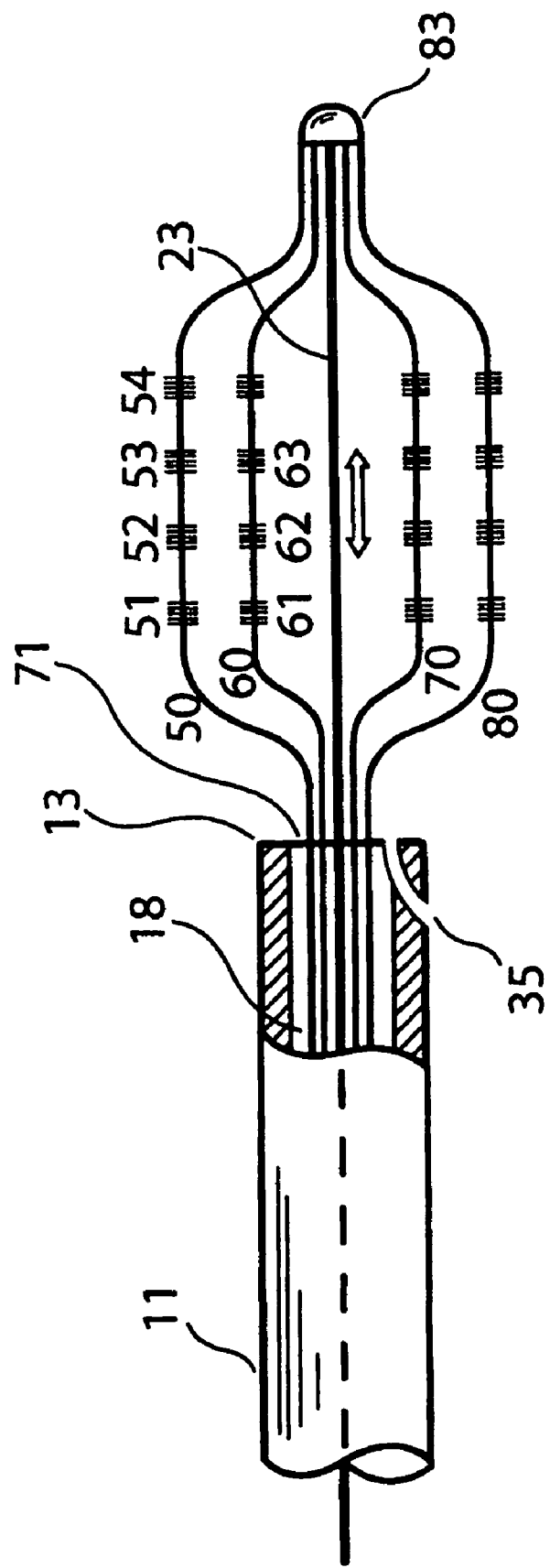
FIG. 8A is one embodiment of a cross-sectional view of the distal end portion of the device system of FIG. 7, the device system having a deployable optical fiber support scaffold structure positioned distal to the distal section of a flexible catheter shaft at a deployed state.

In one preferred embodiment, the optical thermal medical device is a basket catheter. As shown in FIG. 8A, the optical thermal device system may comprise a pulling wire 23 inside the lumen 18 of the catheter shaft 11. The pulling wire or connecting wire 23 has a distal end and a proximal end, wherein the distal end of the pulling wire 23 is joined to the distal joint 83 of the basket fibers, and wherein the proximal end of the pulling wire is secured to the pulling mechanism 16 mounted on the handle 15. The pulling mechanism 16 may be a special push-pull controller or the like on the handle 15 adapted for the push-pull operation of the pulling wire 23. The fiber assembly arrangement, including an optical fiber bundles of fibers 50, 60, 70, 80 with gratings, is mounted at about the distal section 12 of the catheter shaft 11, wherein the fiber assembly arrangement comprises a plurality of preshaped expandable basket fiber members 50, 60, 70, 80, each basket fiber having a fiber distal end and a fiber proximal end, wherein the fiber distal ends of the preshaped expandable basket fibers are joined at a basket distal joint 83. The fiber assembly arrangement is associated the fiber assembly deployment mechanism 17, which is actuatable to deploy the arrangement out of the distal end opening 71 of the catheter shaft 11. Prior to activating the wire 23, the wire 23 is aligned in parallel with the fibers 50, 60, 70, 80. During deployment phase, the fibers are first deployed outside of the distal end 13 of the catheter by a deployment mechanism 17. When the wire 23 is pulled by a pulling mechanism 16 located at the handle 15 of the basket catheter 19 externally, the optical fibers will expand outwardly and form a basket.

Figure 8B:
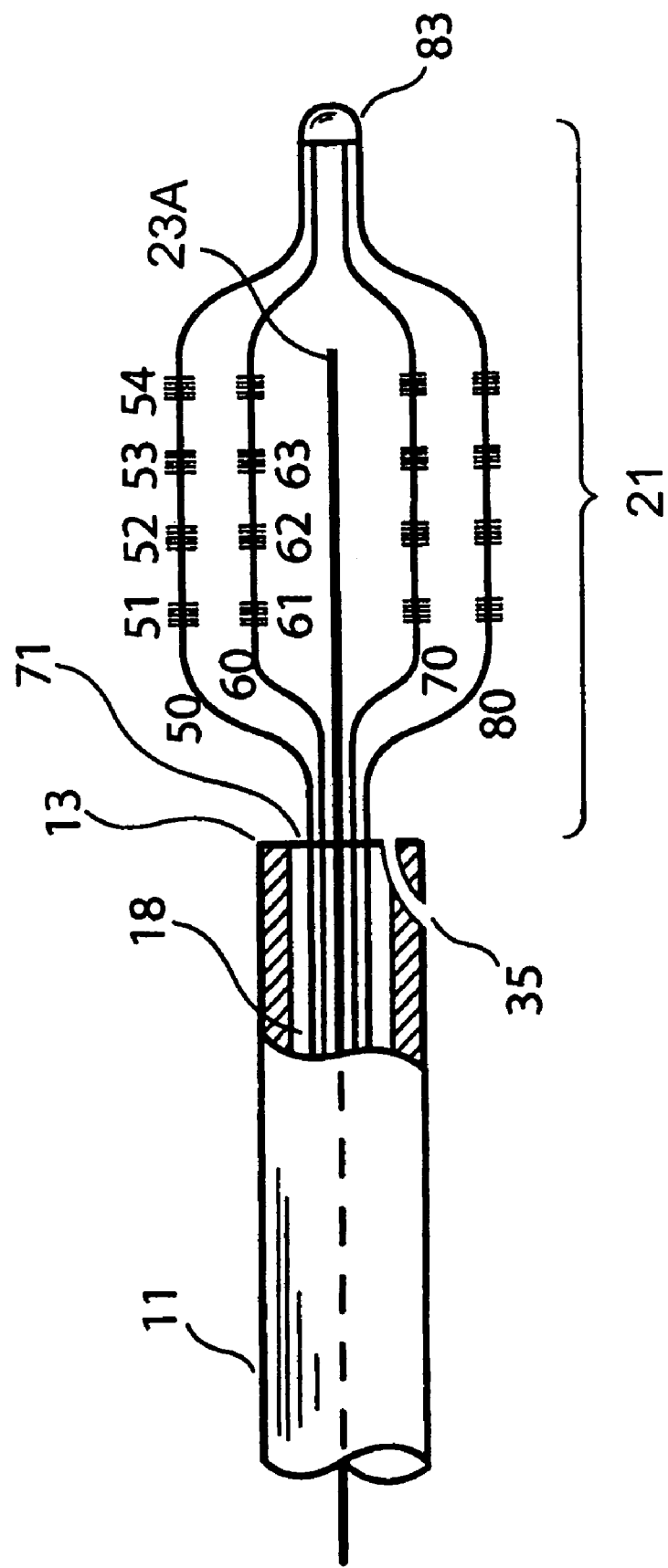
FIG. 8B is another embodiment of a cross-sectional view of the distal end portion of the device system of FIG. 7, the device system having a deployable optical fiber support scaffold structure positioned distal to the distal section of a flexible catheter shaft at a deployed state.

In another embodiment as shown in FIG. 8B, the optical apparatus or device system is a basket type catheter with a support scaffold structure, comprising a middle temperature sensor or optical fiber 23A. The middle optical fiber 23A is located longitudinally at about equal distances from any axial basket members 50, 60, 70, and 80. In one aspect, the device system has a deployable support scaffold structure 21 positioned distal to the distal section of a flexible catheter shaft 11 at a deployed state. In another aspect, the deployment of the support scaffold structure is self-expandable. In one embodiment, the middle optical fiber 23A is configured for emitting adequate and proper light energy enabling desired photodynamic activation onto the surrounding tissue of a blood vessel or body conduit that is photosensitized.

Figure 8C:
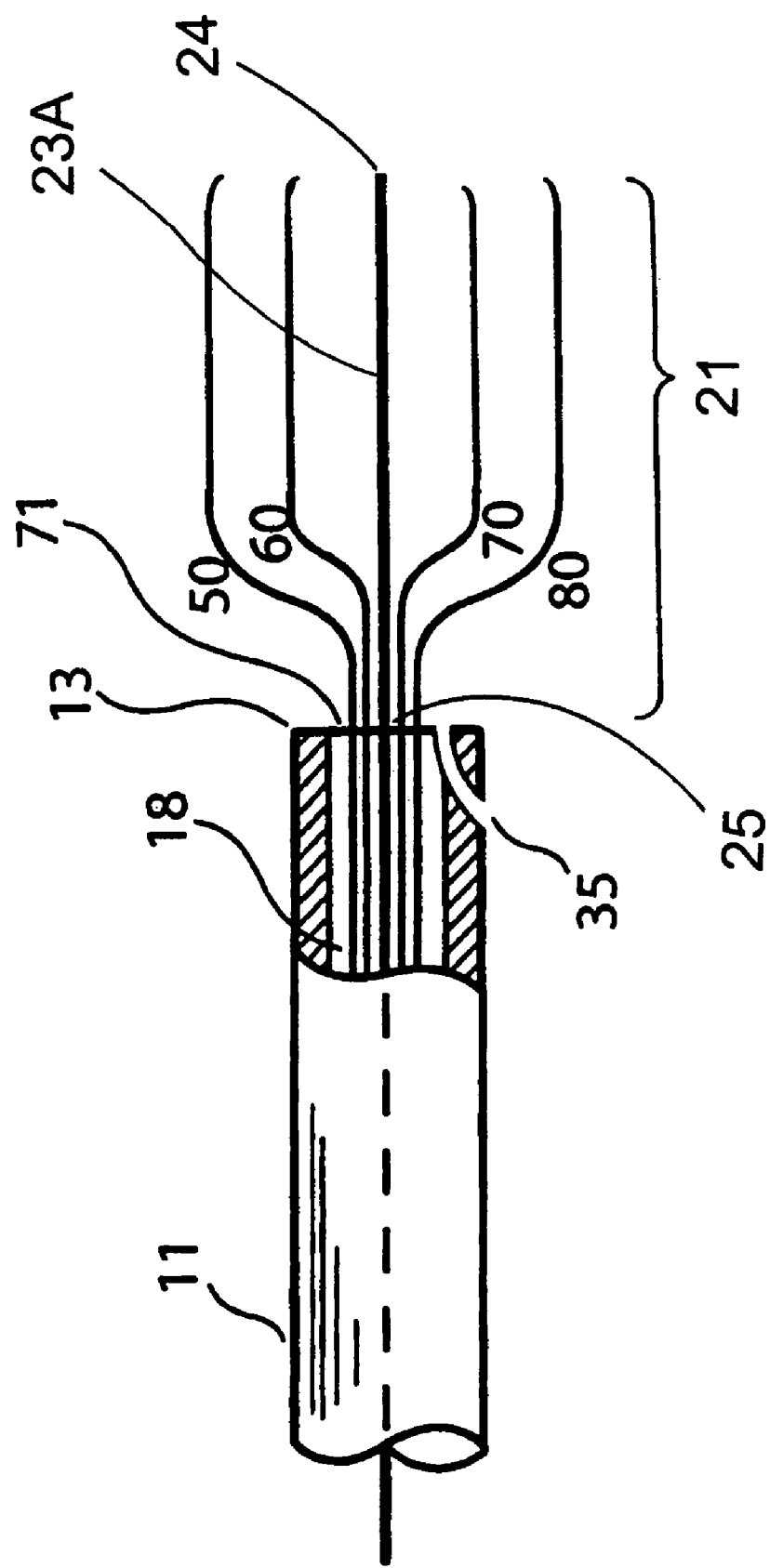
FIG. 8C is one embodiment of a cross-sectional view of the distal end portion of the device system of FIG. 7, the device system having a self-expandable support scaffold structure positioned distal to the distal section of a flexible catheter shaft at a deployed state.

In still another embodiment as shown in FIG. 8C, it shows a cross-sectional view of the distal end portion of the device system of FIG. 7. The device system has a deployable scaffold structure positioned distal to the distal section of a flexible catheter shaft 11 at a deployed state and located at the distal section of the flexible catheter shaft at a pre-deployed state. In one embodiment, the middle optical fiber 23A is configured for emitting adequate and proper light energy enabling desired photodynamic therapy onto the surrounding tissue of a blood vessel or body conduit. Some aspects of the invention relate to an optical apparatus for treating tissue comprising a light emitting optic fiber for providing adequate light energy to initiate photodynamic therapy onto the photosensitized vulnerable plaque, wherein the optic apparatus comprises a support scaffold to stabilize the apparatus and to maintain the emitting optic fiber at essentially the middle of the longitudinal support scaffold structure.

Figure 10:
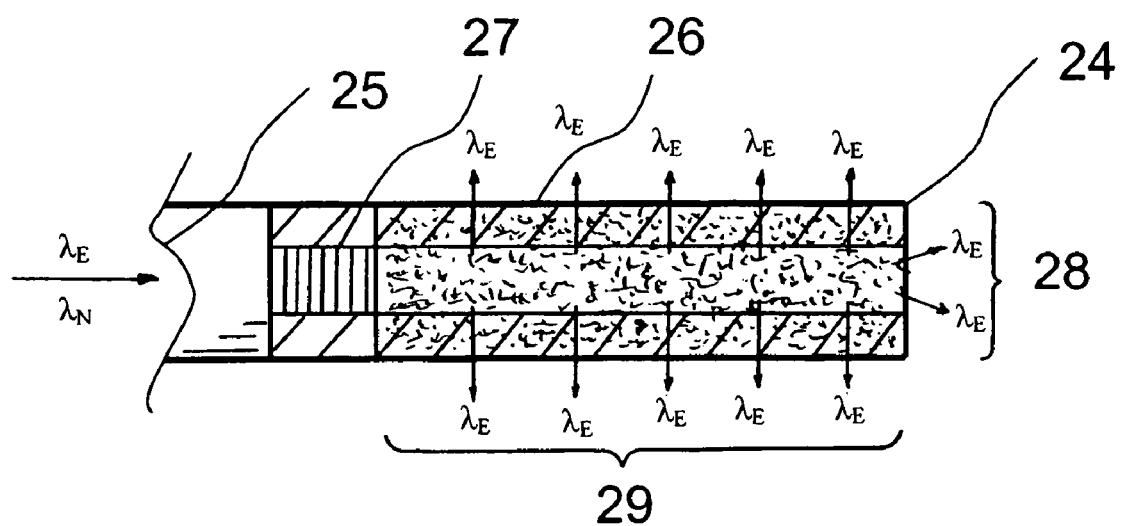
FIG. 10 is a detailed description of the middle fiber component of the support scaffold structure positioned at the distal section of a flexible catheter shaft.

FIG. 10 shows a detailed description of the middle optical fiber 23A of the support scaffold arrangement 21 positioned distal to the shaft distal end 13 of a flexible catheter shaft 11 at a deployed state. In one embodiment, the middle optical fiber 23A comprises a distal end 24 and a proximal end 25 that is optically connected to the light source 98 that has at least one light beam, wherein the light beam is coupled into the middle optical fiber 23A. In a further embodiment, the optical fiber 23A comprises a grated fiber section 27 for monitoring the surrounding temperature or environment conditions and a roughened emitting zone 29 configured for emitting the desired light energy for photodynamic therapy through either the end surface 28 and/or the circumferential surface 26 of the middle fiber 23A.

The emitting zone 29 is generally located at and covers about the axial length of the monitoring fibers on the basket members 50, 60, 70, 80 so as to enable photodynamic therapy once the abnormal temperatures (and hence vulnerable plaque indications) are identified by using the disclosed catheter having dual diagnostic and therapeutic functions. In one alternate embodiment, the emitting zone covers beyond the axial length of the monitoring fibers on the basket members. In some such embodiments, the optical fiber 23A of the support scaffold structure is configured for thermally treating vulnerable plaque in the absence of photosensitizers. In some aspects of the invention, the wavelength of the fiber optic light for temperature sensing is generally in the range of 1 to 2 μm, preferably in the range of 1.3 to 1.6 μm, whereas the wavelength of the fiber optic light for photodynamic therapy is generally in the range of 500 to 800 nm, preferably in the range of 600 to 800 nm. Some aspects of the invention relate to an optical apparatus system having at least one light source having a first light beam with a first wavelength $\lambda_N$ and a second light beam with a second wavelength $\lambda_E$, wherein the first light beam is coupled into the plurality of outer optical fibers and the middle fiber, wherein the at least one optical grating reflects a certain wavelength or intensity of the light beam, the certain wavelength or intensity of the reflected light beam being correlated to known temperature as shown in FIGS. 2 and 4, and wherein the second light beam is coupled into the middle optical fiber for causing photodynamic therapy.

The fiber assembly deployment mechanism 17 is mounted on the handle 15, wherein the fiber assembly deployment mechanism 17 is attached to the proximal end of the fiber bundle. The plurality of preshaped expandable basket fibers is suitably expanded at a deployed state, whereas the plurality of preshaped expandable basket fibers is retracted within the lumen 18 at a non-deployed state. During the insertion into or removal of the medical device from a patient, the fiber assembly arrangement is at a non-deployed state.

In some aspect, the device system further comprises a wire guide shaft at the distal section 12 of the catheter shaft 11, the wire guide shaft defining a wire guide lumen 35, the wire guide shaft having a proximal end and a distal end, wherein the wire guide lumen 35 has at least one opening at the distal end and at least one opening at the proximal end of the wire guide shaft, wherein the wire guide shaft is used for introducing the device system into a vascular vessel over a pre-introduced guidewire. The wire guide lumen 35 may be located close to one side of the wire guide shaft for rapid exchange of the optical fiber device system over the guidewire. For guiding the device system of the present invention into a blood vessel, the distal section 12 may further comprise an externally detectable imaging element, such as an ultrasound transducer, an electromagnetic chip, an MRI coil, a short range radiofrequency antenna, or the like.

Therefore in some aspect, it is provided an optical thermal basket catheter for monitoring temperature of a vessel wall of a patient comprising: (a) an elongate catheter sheath having a lumen, a distal sheath end, and a proximal sheath end; (b) a plurality of optical fibers deployably disposed within the lumen of the catheter sheath, each fiber having a distal fiber portion, a distal fiber end and a proximal fiber end, wherein the plurality of distal fiber portions is suitably expandable in an outwardly radial manner adapted for forming a basket shape and for contacting at least a portion of the vessel wall, each fiber having at least one optical grating along an axis of the fiber; and (c) a light source having a light beam, wherein the light beam is coupled into the plurality of optical fibers, wherein the at least one optical grating reflects a certain wavelength or intensity of the light beam, the certain wavelength or intensity of the reflected light beam being correlated to the temperature of the portion of the vessel wall.

In another preferred embodiment, the optical thermal device for monitoring temperature of a tissue region of a patient is a steerable or flexible probe. The probe comprises an elongate tubular element comprising at least one optical fiber that contacts the tissue region; the at least one optical fiber having at least one optical grating along an axis of the fiber; and a light source having a light beam, wherein the light beam is coupled into the at least one optical fiber; wherein the at least one optical grating along the axis of the fiber reflects a certain wavelength or intensity of the light beam, the certain wavelength or intensity of the reflected light beam being correlated to the temperature of the tissue region.

In some aspect, the elongate tubular element of the probe is a catheter, a cannula, or a hollow needle with side opening. The tissue region of interest comprises a vessel wall of a blood vessel, a heart or a breast of the patient. In another aspect, the optical grating is a long period grating or Bragg grating, wherein the optical grating is coated with a material having a thermal coefficient that is greater than a thermal coefficient of the fiber. The optical thermal device may further comprise an optical diffraction means for simultaneously measuring multiple peaks of the reflected light beam. Typically, the optical grating has a length between 0.2 and 40 mm, whereas the probe has a temperature resolution between 0.001 to 1.0° C.

Figure 9A:
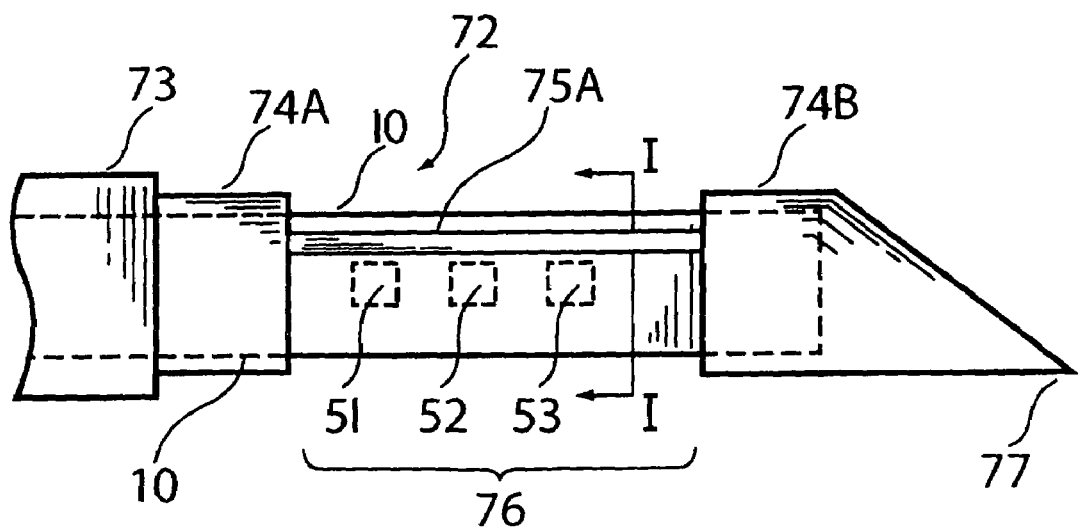
FIG. 9A is one embodiment of a hollow needle probe with side opening.

FIG. 9A shows one embodiment of a hollow needle probe 72 with side opening 76, wherein the surface of an enclosed optic fiber 10 is exposed to and contacts with the surrounding tissue through the opening 76. In a preferred embodiment, the needle probe 72 comprises a handle 73 and a needle body that is hollow, wherein the needle body is comprised of a distal needle portion 74B, a proximal needle portion 74A and at least two connecting bars 75A, 75B securely coupling the distal needle portion 74B and the proximal needle portion 74A. Further, the proximal needle portion 74A is securely attached to the handle 73. The distal needle portion 74B further comprises a penetrating end 77 that is suitably sharpened for easily penetrating into and through tissue, such as a heart or a breast.

Figure 9B:
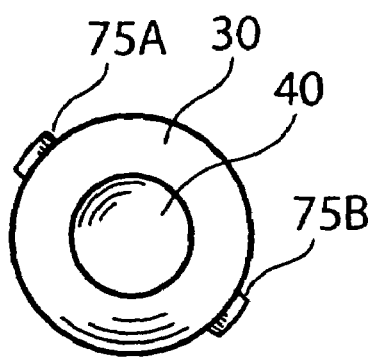
FIG. 9B is a side cross-sectional view of the needle probe, section I—I of FIG. 9A.

Within the hollow cavity of the needle body, there provides an optic fiber 10 with gratings 51, 52, 53. FIG. 9B shows a side cross-sectional view of the needle probe 72, section I—I of FIG. 9A. The optic fiber 10 comprises the cladding 30 and the core 40. In one aspect, the optic fiber is securely held within the needle body in a way such that the surface of the fiber is exposed to a target tissue for mapping the tissue temperature or detecting the diseases, for example, the breast tumor or cancer. In another aspect, the optic fiber 10 is integrated with a light source, a fiber splitting coupler, wavelength diffraction elements, and an optical signal detection system as described above in FIG. 6. In one embodiment, the optic fiber of the needle probe further comprises a section configured for emitting adequate and proper light energy enabling desired photodynamic therapy onto the surrounding tissue. Some aspects of the invention relate to an optical apparatus for treating tissue comprising a light emitting optic fiber for providing adequate light energy to initiate photodynamic therapy onto the photosensitized tumor/cancer, breast tumor, breast cancer, and the like.

The optical fiber sensors system has several operational advantages including immunity to electromagnetic interference, high flexibility, remote sensing capability, smaller size of sensing element, lightweight, and easy to fabricate. It is one preferred aspect of the present invention to provide an optical fiber sensor for chemical composition, stress-strain tissue elasticity, temperature and pressure sensing of the blood vessel wall related to vulnerable plaque.

Photodynamic Therapy

It is one object of the present invention to provide an optical apparatus for treating tissue comprising a light emitting optic fiber for providing desired light energy to initiate photodynamic therapy onto the photosensitized tissue, such as vulnerable plaque. In one embodiment, the optical apparatus has both diagnostic and therapeutic functions. Some aspects of the invention provide an optical apparatus for treating tissue of a patient comprising: an elongate tubular element having a lumen, a distal end, and a proximal end; a support scaffold structure deployable out of the distal end of the tubular element, wherein the support scaffold structure comprises a plurality of basket arms extendable outwardly for fixing/stabilizing the support scaffold in place when deployed, the support scaffold structure having a middle optical fiber that emits light; and a light source having a light beam, wherein the light beam is coupled into the middle optical fiber.

Photodynamic therapy (PDT) is a treatment that uses a drug, called a photosensitizer or photosensitizing agent, and a particular type of light. When photosensitizers are exposed to a specific wavelength of light, they produce a form of oxygen that kills nearby cells. Each photosensitizer is activated by light of a specific wavelength. This wavelength determines how far the light can travel into the body. Thus, doctors use specific photosensitizers and wavelengths of light to treat different areas of the body with PDT. In the first step of PDT for tissue treatment, a photosensitizing agent is injected into the bloodstream. The agent is absorbed by cells all over the body, but may stay in particular cells longer than it does in normal cells. At some specific period after injection, the target tissue is exposed to light. The photosensitizer in the target tissue absorbs the light and produces an active form of oxygen that destroys nearby undesired cells. The light used for PDT can come from a laser or other sources of light. Laser light can be directed through an optical fiber to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer.

U.S. Patent Application publication No. 2004/0092830, entire contents of which are incorporated herein by reference, discloses a catheter for detecting and treating diseased tissue in a blood vessel or other hollow body organ. The catheter comprises an elongated tubular catheter shaft having a distal end comprising a light transmission zone with a diagnostic optical fiber having a distal end terminating within the light transmission zone for emitting and receiving light through the light transmission zone for use in connection with a diagnostic method for detecting diseased tissue.

U.S. Patent Application publication No. 2004/0093044, entire contents of which are incorporated herein by reference, discloses light delivery catheters for use in PDT therapeutic methods that require illumination of target tissue within a blood vessel or other hollow body organ. An improved catheter comprises a catheter shaft having a light treatment zone at its distal end. A light guide, such as an optical fiber, in the catheter shaft transmits light from a light source at the proximal end of the catheter shaft to the light treatment zone. An occlusion balloon is positioned on the distal end of the catheter shaft adjacent to the light treatment zone. The balloon means tends to block the blood flow during treatment and causes undesired side effects.

U.S. Pat. No. 6,096,030, entire contents of which are incorporated herein by reference, discloses a light delivery catheter for use in PDT treatment, including a hollow shaft with a balloon at its distal end. A light guide extends along the sheath and has a light-radiating portion of light source at its end within the balloon. The balloon is positioned at the target site and target tissue is irradiated causing destruction of the target tissue. The balloon means tends to block the blood flow during treatment and causes undesired side effects.

U.S. Patent Application publication No. 2004/0057900, entire contents of which are incorporated herein by reference, discloses detectably labeled macrophage scavenger receptor antagonists useful for the diagnosis and monitoring of vulnerable plaque by administering to a patient a detectably labeled scavenger receptor antagonist and detecting or imaging the location of the pathologies. This invention also provides pharmaceutically acceptable compositions comprising the detectably labeled scavenger receptor antagonists of the present invention.

U.S. Patent Application publication No. 2004/0057900, entire contents of which are incorporated herein by reference, discloses a method of stabilizing a vulnerable plaque in a subject comprising the steps of: a) administering a therapeutically effective amount of at least one photosensitizer composition, wherein the photosensitizer composition is localized to the vulnerable plaque; and b) light activating the photosensitizer composition to produce a phototoxic species; and c) stabilizing the vulnerable plaque against rupture.

U.S. Pat. No. 6,054,449, entire contents of which are incorporated herein by reference, discloses a method for employing photoactivatable compounds for diagnosing such diseases as atherosclerosis, restenosis, cancer, cancer precursors, noncancerous hyperproliferative diseases, psoriasis, macular degeneration, glaucoma and viruses. Photodynamic therapy has been applied in cardiovascular medicine for at least two broad indications: treatment of atherosclerosis and inhibition of restenosis due to intimal hyperplasia after vascular interventions. Hematoporphyrin derivative was the first of a number of photosensitizers with demonstrable, selective accumulation within atheromatous plaques. Subsequent studies have underscored the affinity of porphyrin derivatives for atheromatous plaques in rabbits and miniswine.

A photosensitizer is used in the disclosed methods at a dosage that facilitates the increase of vascular permeability to deliver a drug of interest. A useful dosage of a photosensitizer for the disclosed methods depends, for example, on a variety of properties of the activating light (e.g., wavelength, energy, energy density, and intensity), the optical properties of the target tissue and properties of the photosensitizer. In certain embodiments, photosensitizers useful for the described methods of this invention include, but are not limited to, members of the following classes of compounds: porphyrins, chlorins, bacteriochlorins, purpurins, phthalocyanines, naphthalocyanines, texaphyrines, and non-tetrapyrrole photosensitizers. For example, the photosensitizer may be, but is not limited to, Photofrin, benzoporphyrin derivatives, tin ethyl etiopurpurin (SnET2), sulfonated chloroaluminum phthalocyanines and methylene blue, and any combination of any or all of the above.

A photosensitizer useful for the described methods of the invention may be supplied to the organism of interest by any means known to the skilled artisan including, but not limited to, oral, local, slow release implant, systemic injection (e.g., venous, arterial, lymphatic), local injection (e.g., slow release formulations), hydrogel polymers, inhalation delivery (e.g., dry powder, particulates), electroporation-mediated, iontophoresis or electrophoresis mediated, microspheres or nanospheres, liposomes, erythrocyte shells, implantable delivery devices, local drug delivery catheter, perivascular delivery, pericardial delivery, and eluting stent delivery. A photosensitizer useful for the described methods may be prepared or formulated for supply to the organism of interest in any medium known to the skilled artisan including, but not limited to, tablet, solution, gel, aerosol, dry powder, biomolecular matrix, and inhalation.

As illustrated in U.S. Patent Application publication No. 2004/0071632, entire contents of which are incorporated herein by reference, it is disclosed that IK17 can be labeled with photodynamic compounds that emit energy upon stimulation with an appropriate wavelength of light that can be administered by the use of a catheterized light source of the invention. Activation of the compound may ablate the atherosclerotic plaque or inhibit the growth of the plaque.

Yock at 2003 TCT meeting in Washington, D.C., reported photodynamic modulation of vulnerable plaque with antrin (that is, motexafin lutetium) in animal and clinical studies. Motexafin lutetium is excitable by light at about a wavelength of 740 nm that penetrates tissue and is water soluble with short plasma half life and no significant phototoxicity. Further, it is preferentially absorbed by atheromatous plaque. Animal study data indicate that motexafin lutetium localizes in atheromatous plaque and in intimal hyperplasia, variably reduces plaque in rabbit models of atherosclerosis, reduces intimal hyperplasia in rat models, and consistently depletes macrophages across animal models. The clinical implications are: reducing plaque cellularity would have a positive effect on restenosis; and a preferential uptake by macrophages could mean stabilization of vulnerable plaque. Some aspects of the invention relate to a method of diagnosing and photodynamically treating vulnerable plaque comprising using a basket type support scaffold catheter with light irradiating capability for desired photodynamic therapy.

The radiation used in the described methods, in certain embodiments, is calibrated so that it enhances vascular permeability at the selected site in the organism of interest when applied to the chosen type and dose of photosensitizer. Radiation used in the described methods of the invention is preferably calibrated, for example, by choosing the appropriate wavelength, power, power density, energy density, and time of application relative to the time of supply of the photosensitizer to the organism. In certain embodiments, the radiation wavelength used in the described methods is absorbed by the photosensitizer used. In certain preferred embodiments, the radiation wavelength used in the described methods is such that the absorption coefficient at the chosen wavelength for the photosensitizer used is at least about 20 percent of the highest absorption coefficient for that photosensitizer on the spectrum of electromagnetic radiation of from about 280 nm to about 1700 nm.

Although photodynamic therapy has been extensively researched and is well known to one skilled in the art, none of the prior art teaches a method for simultaneously diagnosing and treating vulnerable plaque via photodynamic therapy using the same catheter or cannula apparatus on a one-step operation. Some aspects of the invention provide a method for treating a tissue region of a patient, the method comprising: a) providing an elongate tubular catheter into contacting the tissue region, wherein the elongate tubular catheter comprises a plurality of peripheral optic fibers in a support scaffold structure and a middle optic fiber, each fiber having at least one optical grating along an axis of the fiber, wherein the middle fiber further comprises a light transmission zone configured for photodynamic therapy; b) monitoring a temperature of the tissue region, wherein a light source having a light beam is coupled into the optical fiber; the at least one optical grating reflecting a certain wavelength or intensity of the light beam, and the certain wavelength or intensity of the reflected light beam being correlated to the temperature; c) administering a therapeutically effective amount of at least one photosensitizer composition, wherein the photosensitizer composition is localized to the tissue region; d) light activating the photosensitizer composition to produce a phototoxic species, wherein the activating light is transmitted from the middle fiber; and f) treating the tissue region photodynamically.

By way of examples, a photosensitizer is administered to a patient under a physician's supervision. An optical apparatus of the invention is inserted into the blood vessel at about the target tissue. The diagnostic function of the apparatus is activated to measure the thermal profiles of the target tissue leading to identifying the vulnerable plaque indication. Once the region of vulnerable plaque at the target tissue is confirmed, the therapeutic function of the apparatus is activated to provide photodynamic light energy to activate the needed photodynamic therapy. The remaining or surrounding tissue outside the irradiation zone would not go through the photodynamic therapy due to the absence of the activating light wavelength. Therefore, the photodynamic treatment is limited to the target tissue locally.

Some aspects of the invention relate to an optical thermal basket catheter for monitoring temperature of a vessel wall of a patient comprising: a) an elongate catheter sheath having a lumen, a distal sheath end, and a proximal sheath end; b) a plurality of outer optical fibers deployably disposed within the lumen of the catheter sheath, each outer fiber having a distal fiber portion, a distal fiber end and a proximal fiber end, wherein the plurality of distal fiber portions is suitably expandable in an outwardly radial manner configured for forming a basket shape and for contacting at least a portion of the vessel wall, each outer fiber having at least one optical grating along an axis of the fiber; c) a longitudinal middle optical fiber spaced about equally from each expanded outer fiber, wherein the middle fiber emits a light energy suitable for photodynamic therapy; and d) a light source having a light beam, wherein the light beam is coupled into the plurality of outer and middle optical fibers, wherein the at least one optical grating reflects a certain wavelength or intensity of the light beam, the certain wavelength or intensity of the reflected light beam being correlated to the temperature of the portion of the vessel wall.

From the foregoing, it should now be appreciated that an optical thermal mapping and therapeutic device comprising at least one optical fiber with at least one optical grating for simultaneously monitoring the thermal distribution of and detecting vulnerable plaque, and treating diseased tissue within a blood vessel has been disclosed. It is also generally applicable for monitoring temperature in a body vessel or channel, in a breast, in a heart, or in other tissue. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An optical apparatus for treating tissue of a patient comprising:
   an elongate tubular element having a lumen, a distal end, and a proximal end;
   a support scaffold structure deployable out of the distal end of the tubular element, wherein the support scaffold structure comprises a plurality of basket arms extendable outwardly for stabilizing said support scaffold in place when deployed, the support scaffold structure having a central optical fiber that emits light, wherein at least one basket arm of the support scaffold structure comprises a peripheral optical fiber that is optically connected to a light source having a light beam, said peripheral optical fiber having at least one optical grating along an axis of said peripheral fiber that reflects a certain wavelength or intensity of said light beam, said certain wavelength or intensity of the reflected light beam being correlated to a temperature, wherein said optical grating is coated with a material having a thermal coefficient that is greater than a thermal coefficient of the fiber; and
   said light source having a light beam, wherein the light beam is coupled into said central optical fiber.

2. The optical apparatus of claim 1, wherein said optical grating is a Bragg grating.

3. The optical apparatus of claim 1, wherein said optical grating is a long period grating.

4. The optical apparatus of claim 1, wherein said optical grating has a length between 0.2 and 40 mm.

5. The optical apparatus of claim 1, wherein said optical apparatus has a temperature resolution between 0.001° C. and 5° C.

6. The optical apparatus of claim 1, wherein said tissue is a vessel wall of a blood vessel.

7. The optical apparatus of claim 1, wherein said tissue is a vulnerable plaque of a blood vessel.

8. The optical apparatus of claim 1, wherein said elongate tubular element is a cannula.

9. The optical apparatus of claim 1, wherein said elongate tubular element is a catheter.

10. The optical apparatus of claim 9, wherein said catheter comprises a wire guide shaft located at a distal section of the catheter, said wire guide shaft being configured for riding said optical apparatus on a guidewire.

11. A method for treating a tissue region of a patient, the method comprising:
   a) providing an elongate tubular catheter into contacting said tissue region, wherein said elongate tubular catheter comprises a plurality of peripheral optic fibers in a support scaffold structure that is radially expandable and a central optic fiber, each fiber having at least one optical grating along an axis of said fiber, wherein the central fiber further comprises a light transmission zone configured for a photodynamic therapy;
   b) monitoring temperature of the tissue region, wherein a light source having a light beam is coupled into said optical fiber; said at least one optical grating reflecting a certain wavelength or intensity of said light beam, and said certain wavelength or intensity of the reflected light beam being correlated to the temperature;
   c) administering a therapeutically effective amount of at least one photosensitizer composition, wherein the photosensitizer composition is localized to the tissue region;
   d) light activating the photosensitizer composition to produce a phototoxic species, wherein the activating light is transmitted from the central fiber; and
   e) treating the tissue region photodynamically.

12. The method of claim 11, wherein said optical grating is a Bragg grating.

13. The method of claim 11, wherein said optical grating is a long period grating.

14. The method of claim 11, wherein said optical grating has a length between 0.2 and 40 mm.

15. The method of claim 11, wherein said optical apparatus has a temperature resolution between 0.001° C. and 5° C.

16. The method of claim 11, wherein said tissue region is a vessel wall of a blood vessel.

17. The method of claim 11, wherein said tissue region is a vulnerable plaque region of a blood vessel.

18. The method of claim 11, wherein said catheter comprises a wire guide shaft located at a distal section of the catheter, said wire guide shaft being configured for riding said optical apparatus on a guidewire.

19. The method of claim 11, wherein said photosensitizer composition is selected from a group consisting of porphyrins, chlorins, bacteriochlorins, purpurins, phthalocyanines, naphthalocyanines, texaphyrines, and combinations thereof.

20. The method of claim 11, wherein said photosensitizer composition is selected from a group consisting of photofrin, benzoporphyrin derivatives, tin ethyl etiopurpurin, sulfonated chloroaluminum phthalocyanines, methylene blue, motexafin lutetium, and combinations thereof.

* * * * *